United States Patent [19]
Christen et al.

[11] Patent Number: 5,750,560
[45] Date of Patent: May 12, 1998

[54] THERAPEUTIC COMPOSITIONS BASED ON 1,2-DITHIOLE-3-THIONE DERIVATIVES

[75] Inventors: Marie-Odile Christen, Paris; Jean-Louis Burgot, Rennes, both of France

[73] Assignee: Laboratoires De Therapeutique Moderne, Suresnes Cedex, France

[21] Appl. No.: 563,034

[22] Filed: Nov. 27, 1995

Related U.S. Application Data

[62] Division of Ser. No. 140,132, Dec. 27, 1993, Pat. No. 5,470,871.

[30] Foreign Application Priority Data

May 2, 1991 [FR] France ................... 91 05411

[51] Int. Cl.⁶ ......................................... A61K 31/385
[52] U.S. Cl. ............................................... 514/441
[58] Field of Search ................................... 514/441

[56] References Cited

PUBLICATIONS

Faust, CA 67:82141s (1967).
Stachel, CA 114:164074a (1991).

*Primary Examiner*—Robert Gerstl
*Attorney, Agent, or Firm*—Young & Thompson

[57] ABSTRACT

The present invention relates to therapeutic compositions based on compounds chosen from the formulae:

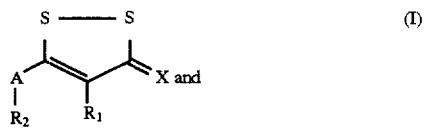

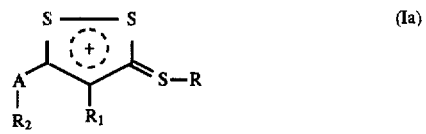

in which:

X is chosen from =S, =O, =SO, =N—OH, =N—$R_5$, =N—NH—$CONH_2$, =N—NH—$CSNH_2$ and

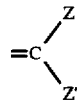

A is chosen from the >C=N—OH group, a group of formula >C=N—$OR_3$, a C=O group, a group C=N—$R_4$ and a CHOH group,
and their pharmaceutically acceptable salts.

These compositions may be used as free-radical trapping agents.

7 Claims, No Drawings

THERAPEUTIC COMPOSITIONS BASED ON 1,2-DITHIOLE-3-THIONE DERIVATIVES

This application is a division of pending application Ser. No. 08/140,132, filed Dec. 27, 1993, now U.S. Pat. No. 5,470,871.

The present invention relates to therapeutic compositions based on 1,2-dithiole-3-thione derivatives.

As prior art, there may be mentioned anethole trithione or 5-(p-methoxyphenyl)-3H-1,2-dithiole-3-thione which is used in therapy as a choleretic (U.S. Pat. No. 2,556,963), and compounds of formula:

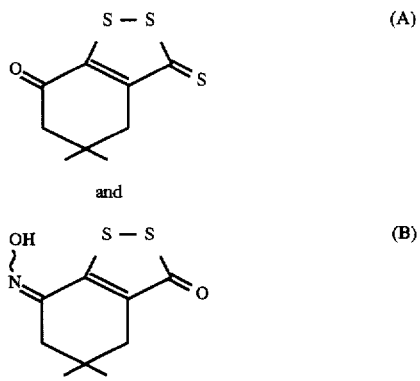

described by Ebel et al., (Bull. Soc. Chim. Fr. 1963, 161), the compound A being obtained by reaction of sulphur with isophorone and the compound B being obtained from the compound A by reaction with $NH_2OH$.

Teicher et al. (Br. J. Cancer, 1990, 62, 17) disclose the use of 1,2-dithiole-3-thiones and in particular 5-(2-thienyl)-1,2-dithiole-3-thione as radioprotectors.

The subject of the present invention is therapeutic compositions containing, as active principle, a compound chosen from compounds of formulae:

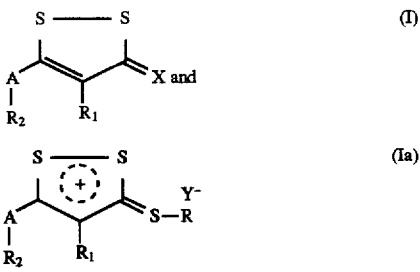

in which

X is chosen from =S, =O, =N—OH, =N—$R_5$, $R_5$ being a $C_1$–$C_6$ alkyl or an aryl group, =N—NH—CO—$NH_2$ and =N—NH—CS—$NH_2$, and

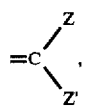

Z and Z' being electron-attracting groups such as ester or cyano groups,

A is chosen from a >C=N—OH group, a group of formula >C=N—$OR_3$, (where $R_3$ is chosen from a $C_1$–$C_6$ alkyl group, a $C_1$–$C_6$ alkyl group substituted with one more groups chosen from hydroxyl, amino, chloro and $C_1$–$C_4$ alkoxy groups, an aryl($C_1$–$C_6$ alkyl) group, a ($C_1$–$C_6$ alkyl)carbonyl group and an aryl($C_1$–$C_6$ alkyl)carbonyl group), a >C=O group, a >C=N—$R_4$ group, $R_4$ being a $C_1$–$C_6$ alkyl group or an aryl group, and a CHOH group, $R_1$ and $R_2$ are chosen, independently of one another, from hydrogen, a halogen, a nitro group, a nitroso group, a thiocyano group, a $C_1$–$C_6$ alkyl group, a $C_2$–$C_6$ alkenyl group, an aryl group, an aryl($C_1$–$C_6$ alkyl) group, an aryl ($C_2$–$C_6$ alkenyl) group, a carboxyl group, a ($C_1$–$C_6$ alkyl)carbonyl group, an arylcarbonyl group, a ($C_1$–$C_6$ alkoxy)carbonyl group, a ($C_1$–$C_6$ alkoxy)carbonyl ($C_1$–$C_6$ alkyl) group, a $C_1$–$C_6$ alkoxy group, a trifluoromethyl group, an amino group, a di($C_1$–$C_6$ alkyl)amino($C_1$–$C_6$ alkyl) group, an acylamino group of formula —$NHCOC_nH_{2n+1}$ with n from 0 to 6, a group —NH—$CSC_nH_{2n+1}$ with n from 0 to 6, a terpenyl group, a cyano group, a $C_2$–$C_6$ alkynyl group, a $C_2$–$C_6$ alkynyl group substituted with a $C_1$–$C_6$ alkyl or an aryl group, a hydroxy($C_1$–$C_6$ alkyl) group, a ($C_1$–$C_6$ acyl) oxy ($C_1$–$C_6$ alkyl) group, a ($C_1$–$C_6$ alkyl) thio group and an arylthio group, or alternatively $R_1$ and $R_2$ together form a mono- or polycyclic $C_2$–$C_{20}$ alkylene group optionally comprising one or more hetero atoms, with the exception of the 2,2-dimethyltrimethylene group, or a $C_3$–$C_{12}$ cycloalkylene group, R is chosen from a $C_1$–$C_6$ alkyl group, Y is a pharmaceutically acceptable anion such as halide or sulphate, and their pharmaceutically acceptable salts.

The present invention relates in particular to a pharmaceutical composition comprising, as active ingredient, a compound chosen from the compounds of formulae:

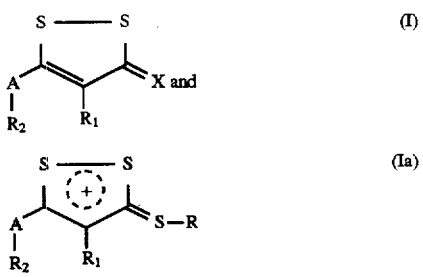

in which:

X is chosen from S and O,

A is chosen from a >C=N—OH group, a group of formula >C=N—$OR_3$, (where $R_3$ is chosen from a $C_1$–$C_6$ alkyl group, a $C_1$–$C_6$ alkyl group substituted with one more groups chosen from hydroxyl, amino, chloro and $C_1$–$C_4$ alkoxy groups, an aryl ($C_1$–$C_6$ alkyl) group, a ($C_1$–$C_6$ alkyl) carbonyl group and an aryl($C_1$–$C_6$ alkyl) carbonyl group), a C=O group, a >C=N—$R_4$ group, $R_4$ being a $C_1$–$C_6$ alkyl group or an aryl group, and a CHOH group, $R_1$ and $R_2$ are chosen, independently of one another, from hydrogen, a halogen, a $C_1$–$C_6$ alkyl group, an aryl group, an aryl ($C_1$–$C_6$ alkyl) group, a carboxyl group, an alkoxy-carbonyl group, a $C_1$–$C_6$ alkoxy group, a trifluoromethyl group, a di($C_1$–$C_6$ alkyl)amino($C_1$–$C_6$ alkyl) group and an acylamino group of formula —$NHCOC_nH_{2n+1}$ with n from 0 to 6, or alternatively $R_1$ and $R_2$ together form a $C_2$–$C_{12}$ alkylene group, with the exception of the 2,2-dimethyltrimethylene group, or a $C_3$–$C_{12}$ cycloalkylene group, R is chosen from a $C_1$–$C_6$ alkyl group, and their pharmaceutically acceptable salts, In the foregoing definition, aryl group or aryl fraction of an arylalkyl group denotes an aromatic carbon-based group such as a phenyl or naphthyl group or an aromatic heterocyclic group such as a thienyl or furyl group, it being possible for these groups to bear one or more substituents chosen from a halogen atom, a $C_1$–$C_4$ alkyl group, a $C_1$–$C_4$ alkoxy group, a trifluoromethyl group, a nitro group and a hydroxyl group.

Some of the compounds of formula I are known.

Thus, Stachel et al. (Arch. Pharm. 1991, 324, 2, 131) describe 1,2-dithiole-3-thiones of formula I in which A=CO, X=S, $R_1$=OCH$_3$ and $R_2$=OCH$_3$ or NH$_2$.

Faust et al., (Z Chem., 1967, 7, 7, 275) describe compounds of formula I in which A=CO, $R_1$=H, X=S and $R_2$=Cl, OC$_2$H$_5$, NH$_2$ or X=O and $R_2$=Cl, OC$_2$H$_5$, NH$_2$, NHC$_6$H$_5$.

In addition, J. Fabian et al. (Chem. Ind. 1966, 1962–3) disclose a 1,2-dithiole-3-thione having the formula I in which X=S, AR$_2$=CO—OC$_2$H$_5$ and R$_1$=H.

Trebaul (Bul. Soc. Chim., 1973, 2, 2, 721) describes compounds of formula I in which A=CO, $R_1$=C$_6$H$_5$, X=S and $R_2$=OC$_2$H$_5$, NH$_2$, N(C$_6$H$_5$)$_2$ or X=O and $R_2$=OC$_2$H$_5$, Cl, p-OCH$_3$C$_6$H$_4$, NH$_2$, NHC$_6$H$_5$, N(C$_6$H$_5$)$_2$.

Moreover, a few compounds of formula I in which A=N—Ar and X=S are described by Quiniou (Bul. Soc. Chem., 1960, 5, 47) and in U.S. Pat. No. 4,190,727.

A first group of compounds of formula I is formed by those in which A is a >C=N—OH group, that is to say oximes of formula

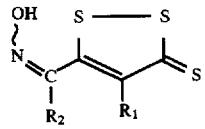

These compounds, which are new, may be prepared according to the invention from 1,2-dithiole-3-thiones of formula:

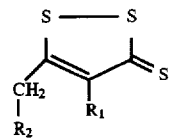

by the action of nitrous acid or isoamyl nitrite.

In practice, a compound of formula III may be reacted with sodium nitrite in a glacial acetic acid medium at approximately 40° C., or isoamyl nitrite in the presence of sodium ethylate in an ethanol medium at 0° C. or at room temperature.

A number of compounds of formula III are known. The others may be prepared according to known processes (see, in particular, Thuillier A., Vialle J., Bull. Soc. Chim. Fr., 1962, 2187, Legrand L., Lozach N., Bull. Soc. Chim. Fr., 1955, 79).

It should be noted that the reaction of sodium nitrite in a glacial acetic acid medium with the compounds of formula III generally leads not only to the formation of the oximes of formula II, but also to the formation of compounds of formula:

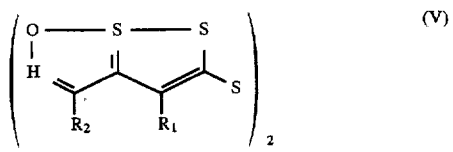

which constitute intermediate products and which yield the oximes of formula II by the action of sodium hydroxide, and also, possibly, of the compounds of formula

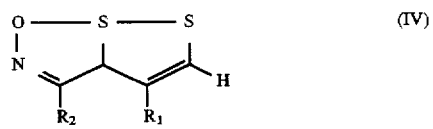

which constitute by-products.

It should also be noted that the reaction of isoamyl nitrite with the compounds of formula III leads only to the formation of oximes of formula II.

A second group of compounds of formula I is formed by those in which A is a >C=O group, that is to say aldehydes or ketones of formula

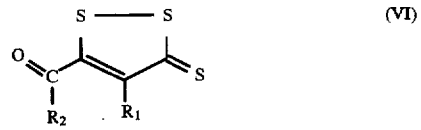

These compounds of formula VI may be prepared by reaction of formaldehyde in an acid medium with an oxime of formula II.

Some of the compounds of formula VI are new. This applies, in particular, to the compounds VIa, corresponding to the formula VI but in which $R_1$ is an alkyl or arylalkyl group or a halogen atom, to the compounds VIb, corresponding to the formula VI but in which $R_1$ is an aryl group and $R_2$ is a hydrogen atom or an alkyl group, and to the compounds VIc, corresponding to the formula VI but in which $R_1$ is a hydrogen atom and $R_2$ is an alkyl group.

A third group of compounds of formula I is formed by those in which A is a group C=N—OR'$_3$ where R'$_3$ is an optionally substituted C$_1$–C$_6$ alkyl group, in particular substituted with one or more groups chosen from hydroxyl, amino, chloro and C$_1$–C$_4$ alkoxy groups, or an aryl (C$_1$–C$_6$ alkyl) group, that is to say compounds of formula

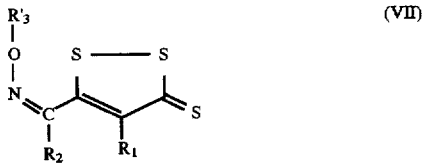

These compounds may be obtained by alkylation of an oxime of formula II using a halide R'$_3$-Hal in the presence of sodium ethylate.

It has, moreover, been discovered that, if an alkylation of an oxime of formula II is performed with a halide R'$_3$-Hal but in the presence of an aqueous sodium hydroxide solution, compounds of formula

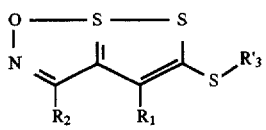
(VIII)

in which R'₃ has the meaning given above, are obtained instead of compounds of formula VII.

It is possible to explain the production of the compounds obtained under these conditions by the fact that the oximes of formula II possess a tautomeric thiol form:

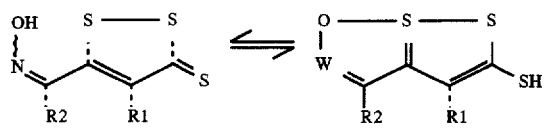

A fourth group of compounds of formula I is formed by the compounds in which A is a group C=N—O—CO—R"₃, R"₃ being chosen from a hydrogen atom, an optionally substituted $C_1$–$C_6$ alkyl group, an aryl group and an aryl ($C_1$–$C_6$ alkyl) group, that is to say compounds of formula

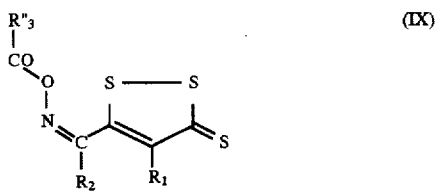
(IX)

in which R"₃ has the meaning given above.

These compounds may be obtained by acylation of an oxime of formula II with an acid chloride R"₃COCl in a toluene medium in the presence of pyridine.

A fifth group of compounds of formula I is formed by the compounds in which A is a CH—OH group, that is to say the compounds of formula

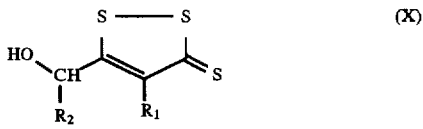
(X)

These compounds may generally be obtained by reduction of a compound of formula VI.

A sixth group of compounds of formula I is formed by the compounds in which A is a group C=N—R₄, R₄ being a $C_1$–$C_6$ alkyl or an aryl group, that is to say compounds of formula

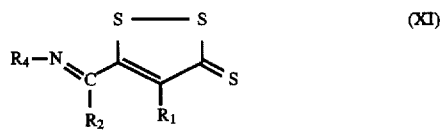
(XI)

These compounds may be obtained from the compounds of formula VI by the action of an amine of formula R₄—NH₂.

A seventh group of compounds of formula I is formed by the compounds in which A is a C=O group and X is an oxygen atom, that is to say compounds of formula:

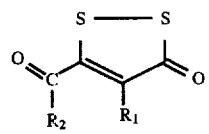
(XII)

in which R₁ and R₂ have the meaning given above. These compounds may be obtained from the compounds of formula VI by the action of benzonitrile oxide.

More generally, the compounds of formula I in which X=O may be obtained from the compounds of formula I in which X=S by the action of benzonitrile oxide.

The oximes of formula VI can, in addition, react in the cold state with methyl acetylenedicarboxlyate in acetone solution according to Davy and Decrouen (Bull. Soc. Chim., 1976, 115) to give compounds of formula

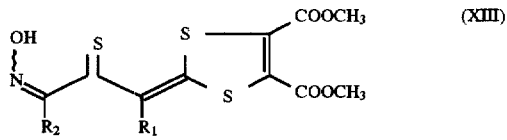
(XIII)

The compounds of formula Ia may be obtained from the compounds of formula I by reaction with an alkyl iodide of formula RI, R being a $C_1$–$C_6$ alkyl group.

The examples which follow illustrate the present invention.

I—Preparation of the oximes of formula II, the disulphides of formula V and the oxadithiazapentalenes of formula IV 1—Use of sodium nitrite in a glacial acetic acid medium.

EXAMPLE

In a 250-ml Erlenmeyer flask equipped with a magnetic stirrer, 1 g of 4,5-dimethyl-1,2-dithiole-3-thione is dissolved in 30 ml of glacial acetic acid brought to the boil. The mixture is allowed to cool to 40° C. 2 g of sodium nitrite in the solid state are added in small portions. An ochre precipitate forms immediately. After 30 min, the acetic acid solution is diluted with water. The copious precipitate, consisting essentially of the disulphide of formula V and traces of the starting 1,2-dithiole-3-thione, is filtered off. The precipitate is added to 20% sodium hydroxide solution. After stirring at 60° C. for 2 hours, almost complete dissolution has taken place with a change in colour. The aqueous solution becomes dark brown. It is extracted with toluene and is then acidified with cooling. A precipitate of the crude, orange-yellow oxime appears. The remaining, unprecipitated oxime is extracted either with sulphuric ether solution or with a dichloromethane solution containing 5% of acetone.

Furthermore, the acetic acid solution obtained after filtering off the crude oxime is extracted with a toluene solution which is combined with that used for extraction of the sodium hydroxide phase. The toluene solution is washed with water, dried over sodium sulphate, concentrated and chromatographed on silica gel. The oxadithiazapentalene is eluted after the starting dithiolethione with toluene.

The structure of the oximes of formula II is determined from a study of the $^1$H and $^{13}$C NMR, IR and mass spectra and from the microanalyses. Assignment of the syn and anti structures for the oxime whose preparation is described above is performed on the basis of the values of the coupling constants $J^1$(C-H) in the arrangements below:

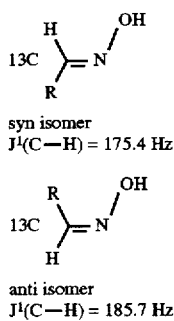

syn isomer
$J^1(C-H) = 175.4$ Hz anti isomer
$J^1(C-H) = 185.7$ Hz

The characteristics of the products obtained, as well as those of other products of formulae II, IV and V, are collated in Tables I and II.

TABLE I

| | | Oximes of formula II | | | Oxadithiaza-pentalenes of formula IV | | |
|---|---|---|---|---|---|---|---|
| R$_1$ | R$_2$ | Code | Yld % | M.p. °C. | Code | Yld % | M.p. °C. |
| CH$_3$ | H | 1 | 65 syn (P*) + anti | 174 | 21 | 30 | 117 |
| CH$_3$ | CH$_3$ | 2 | 50 syn (P*) + anti | 138 | 22 | 40 | 120 |
| H | H | 2 | 20 | 143 | 23 | 10 | 83 |
| H | C$_6$H$_5$ | 4 | 30 | 165 | 24 | 15 | 118 |
| OCH$_3$ | H | 5 | 30 | 108 | | | |
| H | | 6 | 20 | 142 | | | |
| | H | 7 | 15 | 139 | | | |
| H | CH$_3$ | 8 | 55 | 181 | 25 | 30 | 93 |
| C$_2$H$_5$ | CH$_3$ | 9 | 50 | 92 | 26 | 20 | 90 |
| CH$_3$ | CH$_3$CHCH$_3$ | 10 | 45 | 113 | 27 | 30 | 160 |

(*)P: preponderant

TABLE II

| | | Oximes of formula II | | | Dimers of formula V | | |
|---|---|---|---|---|---|---|---|
| R$_1$ | R$_2$ | Code | Yld % | M.p. °C. | Code | Yld % | M.p. °C. |
| | —(CH$_2$)$_3$— | 11 | 50 | 195 | 31 | 25 | 120–21 |
| C$_6$H$_5$ | CH$_3$ | 12 | 55 | 163 | 32 | 25 | 181–82 |
| C$_6$H$_5$ | C$_6$H$_5$ | 13 | 20 | 171 | 33 | 30 | 190–91 |
| COOC$_2$H$_5$ | C$_6$H$_5$ | 14 | 40 | 194 | 34 | 25 | 163–64 |
| CH$_2$C$_6$H$_5$ | H | 15 | 80 | 143 | 35 | 15 | 106–8 |
| CH$_2$C$_6$H$_5$ | CH$_3$ | 16 | 50 | 122 | | | |
| H | C$_2$H$_5$ | 17 | 55 | 130 | 36 | 30 | 143–155 |
| C$_6$H$_5$ | CH$_2$C$_6$H$_5$ | 18 | 40 | 157 | 37 | 20 | 102–103 |
| C$_2$H$_5$ | H | 19 | 50 | 149–160 | | | |
| Cl | H | 20 | 45 | 230 | | | |

2 - Use of isoamyl nitrite.

EXAMPLE

An ethanolic solution of 5-methyl-1,2-dithiole-3-thione (1 equivalent) is added in the course of ½ hour with an equivalent amount of isoamyl nitrite at room temperature to an ethanolic solution containing two equivalents of sodium ethylate. The mixture is left stirring overnight. It is poured into water and the oxime (compound 3) is extracted with an ethyl ether solution. The ethereal solution is washed with water, dried over sodium sulphate, concentrated and purified by chromatography on silica gel. The oxime is eluted after the starting dithiolethione, approximately 40% of the initial amount of which is recovered.

II—Preparation of the compounds of formula VI

EXAMPLE 2 g of dithiolethione oxime of formula II are brought into contact with 25 ml of 37% aqueous formal-dehyde solution acidified with a few drops of concentrated hydrochloric acid and 100 ml of toluene. The mixture is brought to reflux while stirring for 2 hours. The toluene solution very soon becomes dark red.

After cooling and when settling has taken place, the toluene phase is separated, washed with water to neutrality, dried over sodium sulphate, concentrated and chromatographed on silica gel. The dithiolethione aldehydes or ketones of formula VI are eluted with a 60:40 petroleum ether/toluene mixture.

Their structures are established on the basis of conventional techniques of structural analysis, including the use of elemental analysis. In particular, in IR spectroscopy, these compounds all display a $v_{c=o}$ band. Their characteristics are given in Table III.

TABLE III

| Code | R$_1$ | R$_2$ | M.p. °C. | $v_{c=o}$ (cm$^{-1}$) |
|---|---|---|---|---|
| 41 | CH$_3$ | H | 105 | 1660 |
| 42 | C$_6$H$_5$ | H | 132 | 1625 |
| 43 | —CH$_2$—CH$_2$—CH$_2$— | | 95 | 1670 |
| 44 | CH$_3$ | CH$_3$ | 76 | 1690 |
| 45 | H | H | 100 | 1670 |
| 46 | C$_6$H$_5$ | CH$_3$ | 86 | 1670 |
| 47 | OCH$_3$ | H | 101 | 1660 |
| 48 | H | CH$_3$ | 115 | 1660 |
| 49 | CH$_2$C$_6$H$_5$ | H | 124 | 1665 |
| 50 | C$_2$H$_5$ | CH$_3$ | 125 | 1670 |
| 51 | CH$_3$ | CH$_3$—CH—CH$_3$ | 59 | 1690 |
| 52 | CH$_2$C$_6$H$_5$ | CH$_3$ | 63 | 1670 |
| 53 | H | CH$_2$—CH$_3$ | 116 | 1680 |
| 54 | C$_2$H$_5$ | H | 75–76 | 1675 |
| 55 | Cl | H | 136 | 1680 |

III—Preparation of the compounds of formula VII 1 equivalent of the oxime II 1 in ethanolic solution is added in the course of ½ hour to an ethanolic solution containing 2 equivalents of sodium ethylate while cooling externally with a bath of ice-cold water. 1.1 equivalents of methyl iodide are then added. The mixture is left stirring at room temperature for about 15 hours. The solution is then diluted with water and extracted with toluene and the toluene solution is dried over sodium sulphate and concentrated.

The residue is chromatographed on silica gel.

5-Methoxyiminomethyl-4-methyl-1, 2-dithiole-3-thione (VII 1) is eluted with a petroleum ether/toluene (90:10) mixture.

It is a red solid, m.p. 93°–94° C. $^1$H NMR (300 MHz) (CDCl$_3$) δ ppm/TMS=H (s:8.30); OCH$_3$ (s:4.10); CH$_3$ (s:2.30).

IV—Preparation of the compounds of formula VIII

The oxime II is dissolved in 10% aqueous sodium hydroxide solution; an excess of methyl iodide is added in the cold state and the mixture is left stirring at room temperature overnight.

It is then extracted with a toluene solution, which is washed with water, dried, concentrated and chromatographed on silica gel.

The 5-(methylthio)oxadithiazapentalenes VIII are eluted with a petroleum ether/toluene (60:40) mixture.

The characteristics of compounds of formula VIII are collated in Table IV.

TABLE IV

| Code | R$_1$ | R$_2$ | R'$_3$ | M.p. °C. | δppm/ CDCl$_3$ methylthio |
|------|-------|-------|--------|----------|-----------|
| 61 | CH$_3$ | H | CH$_3$ | 115 | 2.79 |
| 62 | C$_6$H$_5$ | H | CH$_3$ | 118 | 2.70 |
| 63 | —CH$_2$—CH$_2$—CH$_2$— | | CH$_3$ | 114 | 2.75 |
| 64 | CH$_3$ | CH$_3$ | CH$_3$ | 107 | 2.70 |
| 65 | H | H | CH$_3$ | 106 | 2.79 |
| 66 | C$_6$H$_5$ | CH$_3$ | CH$_3$ | 160 | 2.60 |
| 67 | C$_6$H$_5$ | C$_6$H$_5$ | CH$_3$ | 201 | 2.60 |
| 68 | COOC$_2$H$_5$ | C$_6$H$_5$ | CH$_3$ | 135 | 2.83 |
| 69 | OCH$_3$ | H | CH$_3$ | 109 | 2.68 |
| 70 | H | CH$_3$ | CH$_3$ | 109 | 2.73 |
| 71 | CH$_2$C$_6$H$_5$ | H | CH$_3$ | 110 | 2.72 |
| 72 | CH$_3$CH$_2$ | CH$_3$ | CH$_3$ | 101 | 2.80 |
| 73 | CH$_3$ | CH$_3$—CH—CH$_3$ | CH$_3$ | 99 | 2.80 |
| 74 | C$_6$H$_5$ | CH$_3$ | CH$_3$ | 119 | 2.64 |
| 75 | H | CH$_2$—CH$_3$ | CH$_3$ | 80 | 2.74 |
| 76 | CH$_3$ | H | C$_2$H$_5$ | 100–102 | 3.18 |
| 77 | CH$_3$ | H | CH$_2$C$_6$H$_5$ | 136 | 4.38 |

V—Preparation of the compounds of formula IX 1.1 equivalents of acetyl chloride are added to a toluene solution containing 1 equivalent of dithiolethione oxime II and a few drops of pyridine while cooling externally with a bath of ice-cold water. Stirring is maintained for 2 hours, the above solution is then poured into water and the product is extracted with toluene. The toluene solution is then washed with water, dried over sodium sulphate, filtered and concentrated and the residue is chromatographed on silica gel. The O-acyldithiolethione oximes IX are eluted with toluene.

The characteristics of the compounds of forumla IX are collated in Table V.

TABLE V

| Code | R$_1$ | R$_2$ | R"$_3$ | Yield | M.p. °C. |
|------|-------|-------|--------|-------|----------|
| 81 | CH$_3$ | H | CH$_3$ | 50% | 127 |
| 82 | C$_6$H$_5$ | H | CH$_3$ | 55% | 164 |

VI—Preparation of the compounds of formula X 1 g of 5-acetyl-4-methyl-1,2-dithiole-3-thione is dissolved in 150 cm$^3$ of absolute ethanol. The mixture is cooled externally with a bath of ice-cold water and an excess of cyanoborohydride is then added. The mixture is allowed to return to room temperature and stirring is continued for about ten hours.

The solution is concentrated to dryness. The residue is then taken up after cooling with a few ml of dilute hydrochloric acid solution. The precipitate and the solution are treated with toluene. The dithiolethione alcohol does not dissolve. It is purified by chromatography on silica gel. It is transferred to the column after dissolution in the minimum amount of ethyl acetate; it is eluted with an ethyl acetate/toluene (30:70) mixture. 5-(1-Hydroxyethyl)-4-methyl-1,2-dithiole-3-thione is obtained in the form of light yellow crystals, m.p. 79°–80° C. (benzene).

VII—Preparation of the compounds of formula XI

An equimolar mixture of aniline and dithiolethione oxime II 1 is brought to reflux for 3 hours in absolute ethanol. The solution blackens immediately. The ethanolic solution is concentrated to dryness. The residue is chromatographed on silica gel. 5-Phenyliminomethyl-4-methyl-1,2-dithiole-3-thione takes the form of black crystals, m.p. 124°–125° C. (petroleum ether).

VIII—Preparation of the compounds of formula XII

The procedure of BOBERG and KNOOP (LIEBIGS ANN. CHEM. 1967, 708, 148) is used:

1 g of 5-formyl-4-methyl-1,2-dithiolethione and 1 g of benzohydroxamoyl chloride (G. W. Perold, A. P. Steyn and F. K. V. von Reiche, J. Am. Chem. Soc. 1957, 79, 462) are dissolved in a minimum amount of dry toluene. Triethylamine is added dropwise and with stirring until the formation of triethylamine hydrochloride is complete. During this addition, the mixture is maintained at room temperature. The initially dark red solution becomes colourless. Stirring is continued for 3 h, the hydro-chloride is then filtered off and the filtrate is concentrated to dryness. The residue is taken up with 100 cc of xylene and the mixture is brought to reflux for 3 h. It is concentrated to dryness; the residue is crystallised in methanol. 5-Formyl-4-methyl-1,2-dithiol-3-one is a colourless solid, m.p. 84° C., yld=65% (C=O KBr 1640 cm$^{-1}$).

IX—Preparation of the compounds of formula XIII

Equivalent amounts of 5-formyl-4-methyldithiolethione oxime and methyl acetylenedicarboxylate are dissolved in the minimum amount of dry acetone. After the mixture has stood for about twenty hours, the addition compound of formula XIII, 3-(4,5-dimethoxycarbonyl-1,3-dithiol-2-ylidene)-2-thioxobutanal oxime, crystallises; it is filtered off and crystallised again in acetone; m.p. 139° C., dark red crystals, IR: OH 3210 cm$^{-1}$ broad band; C=O 1720–1740 cm$^{-1}$. $^1$H NMR (C$_3$D$_6$O) ppm: OH (s:10.68); H(CH) (s:8.42) CH$_3$ (s:2.82); CH$_3$ (COO CH$_3$) (s:3.92 and 4).

X—Preparation of the compounds of formula Ia

Example: Preparation of 5-formyl-4-methyl-3-methylthio-1,2-dithiolylium iodide

5-Formyl-4-methyl-1,2-dithiole-3-thione is dissolved in an excess of methyl iodide.

The mixture is left standing for several days; the dithiolylium ion crystallises out.

The product is filtered off and recrystallised in benzene.

5-Formyl-4-methylthio-1,2-dithiolylium iodide, m.p. 140°–142° C., is thereby obtained.

XI—Preparation of the compounds of formula III

EXAMPLE A

Preparation of 5-ethyl-4-phenyl-1,2-dithiole-3-thione:

This is obtained from commercial 1-phenyl-2-butanone (Aldrich, 98% pure) by applying the method of Thuillier and Vialle (Bull. Soc. Chim. Fr. 1962, 2187).

1,1-Bis(methylthio)-2-phenyl-1-penten-3-one, obtained by condensation of carbon disulphide with the above ketone in the presence of sodium tert-amylate followed by methylation with methyl iodide (Yld=80%), is treated with phosphorus pentasulphide in xylene solution. The dithiolethione is isolated according to the usual method (cooling, washing with sodium hydroxide solution and then with water to neutrality, drying over sodium sulphate, concentration and chromatography). Yield of the sulphuration=70%.

The product is in the form of orange-coloured crystals; m.p. 64° C. (benzene).

$^1$H NMR (CDCl$_3$, δppm/TMS): 1.35 (t, 3H); 2.65 (q, 2H); 7.25 to 7.65 (m, 5H).

EXAMPLE B

Preparation of 5-propyl-1,2-dithiole-3-thione:

This is obtained by sulphuration of ethyl butyrylacetate (Aldrich commercial product, 98% pure) according to the process of L. Legrand and N. Lozac'h (Bull. Soc. Chim. Fr, 195, 79).

A suspension of 0.061 mol of phosphorus pentasulphide and 0.26 mol of sulphur in 250 cm$^3$ of dry xylene is brought to reflux. A solution of 0.13 mol of ethyl butyrylacetate in 30 cm$^3$ of dry xylene is added dropwise. The mixture is left under reflux for 15 to 30 minutes. After cooling, the xylene solution is washed with dilute sodium hydroxide solution and then with water to neutrality. After drying over sodium sulphate, the 5-propyl-1,2-dithiole-3-thione is purified by chromatography on activated neutral alumina (Yld=70%); it is a dark red liquid. $^1$H NMR (CDCl$_3$, δppm/TMS): 1.10 (t, 3H); 1.87 (m, 2H) 2.83 (t, 2H); 7.23 (s, 1H).

The characteristics of dithiolethiones of formula III are given below.

It was found that the compounds of formula I possessed advantageous pharmacological properties and could be used in therapy.

The compounds of formulae II and VI have substantial antimicrobial activity;

The compounds of formula II have significant action on calcium and potassium channels and, as a result, exhibit, inter alia, activity in the cardiovascular field and in gastroenterology, as well as an action on the central nervous system and the respiratory system.

In addition, some of them are antihypertensives or β-blockers and are active with respect to the respiratory system, more especially at tracheal level, and have antiallergic properties due to their broncho-relaxant action.

The products of the invention possess, considering all groups collectively, platelet aggregation-inhibitory properties.

In addition, the compounds of formula I have been shown to be free-radical scavenger agents. They can, as a result, find application as anti-inflammatory, anti-atheroma and anti-ischaemic agents, for combatting ageing, for protecting the liver, as a radioprotective and anticarcinogenic agent, in gasteoenterology, at cardiovascular, respiratory and central level, and more generally as antioxidants.

Results of toxicological studies performed in mice are given below.

Furthermore, the compounds of formula I exert an effect on glutathione and glutathione-dependent enzymes, and give rise to corresponding therapeutic properties (detoxification , anticarcinogenic power). In addition, the compounds of formula I were shown to be immunomodulatory.

TOXICITY OXIMES OF FORMULA II

| | | | Toxicity in mg/kg | |
|---|---|---|---|---|
| $R_1$ | $R_2$ | Code | ip (mouse) | po (mouse) |
| —(CH$_2$)$_3$— | | 11 | 200 | 300 |
| H | H | 3 | 50 | 100 |
| H | C$_6$H$_5$ | 4 | 100 | 300 |

| | $R_1$ | $R_2$ | Colour | M.p. °C. | Crystallisation solvent |
|---|---|---|---|---|---|
| 5-Ethyl-4-phenyl-1,2-dithiole-3-thione | C$_6$H$_5$ | CH$_3$ | Orange crystals | 64 | Benzene |
| 4-Methoxy-5-methyl-1,2-dithiole-3-thione | CH$_3$O | H | Yellow crystals | 51 | Petroleum ether |
| 5-Isobutyl-4-methyl-1,2-dithiole-3-thione | CH$_3$ | CH$_3$—CH—CH$_3$ | Orange-yellow crystals | 50 | Petroleum ether |
| 4-Phenyl-5-(2-phenylethyl)-1,2-dithiole-3-thione | C$_6$H$_5$ | C$_6$H$_5$CH$_2$ | Orange-red crystals | 101 | Methanol |
| 5-Benzyl-4-ethoxycarbonyl-1,2-dithiole-3-thione | COOEt | C$_6$H$_5$ | Light brown crystals | 37 | Benzene |
| 5-(α-thienylmethyl)-1,2-dithiole-3-thione | H | (thienyl) | Yellow crystals | 98 | Cyclohexane |
| 4-Benzyl-5-ethyl-1,2-dithiole-3-thione | C$_6$H$_5$CH$_2$ | CH$_3$ | Yellow liquid* | | |
| 5-Propyl-1,2-dithiole-3-thione | H | CH$_3$CH$_2$ | Red liquid* | | |

*Liquids not distilled

TOXICITY OXIMES OF FORMULA II

| | | | Toxicity in mg/kg | |
|---|---|---|---|---|
| $R_1$ | $R_2$ | Code | ip (mouse) | po (mouse) |
| $C_2H_5$ | $CH_3$ | 9 | >100 | 300 |
| H | $C_2H_5$ | 17 | 100 | 300 |
| $OCH_3$ | H | 5 | 50 | 50 |

TOXICITY KETONES OF FORMULA VI

| | | | Toxicity in mg/kg | |
|---|---|---|---|---|
| $R_1$ | $R_2$ | Code | ip (mouse) | po (mouse) |
| $CH_3$ | H | 41 | 100 | 100 |
| $CH_3$ | $CH_3$ | 44 | 300 | >300 |
| $C_2H_5$ | $CH_3$ | 50 | 100 | >300 |

The therapeutic compositions according to the invention may be administered to man or animals orally or parenterally.

They can be in the form of solid, semi-solid or liquid preparations. As an example, tablets, hard gelatin capsules, suppositories and injectable solutions or suspensions may be mentioned, as well as retard forms and slow-release implanted forms.

In these compositions, the active principle is generally mixed with one or more customary, pharmaceutically acceptable excipients which are well known to a person skilled in the art.

The amount of active principle administered naturally depends on the patient who is being treated, the administration route and the severity of the disease.

We claim:

1. Pharmaceutical composition comprising, as active principle, a compound of formula

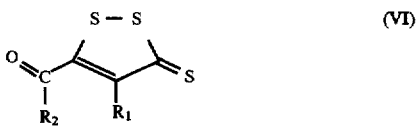

(VI)

in which $R_1$ is chosen, from hydrogen, a halogen, a nitro group, a nitroso group, a thiocyano group, a $C_1$–$C_6$ alkyl group, a $C_2$–$C_6$ alkenyl group, an aryl group, an aryl ($C_1$–$C_6$ alkyl) group, an aryl ($C_2$–$C_6$ alkenyl) group, a carboxyl group, a ($C_1$–$C_6$ alkyl) carbonyl group, an arylcarbonyl group, a ($C_1$–$C_6$ alkoxy)carbonyl group, a ($C_1$–$C_6$ alkoxy) carbonyl ($C_1$–$C_6$ alkyl) group, a $C_1$–$C_6$ alkoxy group, a trifluoromethyl group, an amino group, a di ($C_1$–$C_6$ alkyl) amino ($C_1$–$C_6$ alkyl) group, an acylamino group of formula —NHCOC$_n$H$_{2n+1}$ with n from 0 to 6, a group —NH—CSC$_n$H$_{2n+1}$ with n from 0 to 6, a terpenyl group, a cyano group, a $C_2$–$C_6$ alkynyl group, a $C_2$–$C_6$ alkynyl group substituted with a $C_1$–$C_6$ alkyl or an aryl group, a hydroxy ($C_1$–$C_6$ alkyl) group, a ($C_1$–$C_6$ acyl)-oxy($C_1$–$C_6$ alkyl) group, a ($C_1$–$C_6$ alkyl)thio group and an arylthio group, $R_2$ is chosen from a nitro group, a nitroso group, a thiocyano group, a $C_1$–$C_6$ alkyl group, a $C_2$–$C_6$ alkenyl group, an aryl group, an aryl ($C_1$–$C_6$ alkyl) group, an aryl ($C_1$–$C_6$ alkenyl) group, a carboxyl group, a ($C_1$–$C_6$ alkyl)carbonyl group, an arylcarbonyl group, a ($C_1$–$C_6$ alkoxy)carbonyl group, a ($C_1$–$C_6$ alkoxy)carbonyl ($C_1$–$C_6$ alkyl) group, a trifluoromethyl group, a di($C_1$–$C_6$ alkyl)amino($C_1$–$C_6$ alkyl) group, an acylamino group of formula —NHCOC$_n$H$_{2n+1}$ with n from 0 to 6, a group —NH—CSC$_n$H$_{2n+1}$ with n from 0 to 6, a terpenyl group, a cyano group, a $C_2$–$C_6$ alkynyl group, a $C_2$–$C_6$ alkynyl group substituted with a $C_1$–$C_6$ alkyl or an aryl group, a hydroxy ($C_1$–$C_6$ alkyl) group, a ($C_1$–$C_6$ acyl)-oxy($C_1$–$C_6$ alkyl) group, a ($C_1$–$C_6$ alkyl)thio group and an arylthio group, or alternatively $R_1$ and $R_2$ together form a mono- or polycyclic $C_2$–$C_{20}$ alkylene group optionally comprising one or more hetero atoms, with the exception of the 2,2-dimethyltrimethylene group, or a $C_3$–$C_{12}$ cycloalkylene group.

2. A composition according to claim 1 in which $R_2$ is chosen from $C_1$–$C_6$ alkyl, $C_2$–$C_6$ alkenyl, aryl, aryl($C_1$–$C_6$ alkyl), aryl $C_2$–$C_6$ alkenyl, terpenyl, $C_2$–$C_6$ alkynyl, $C_2$-$C_6$ alkynyl substituted with $C_1$–$C_6$ alkyl or aryl.

3. A composition according to claim 1 in which R is chose from $C_1$–$C_6$ alkyl.

4. Composition according to claim 1, comprising, as active principle, a compound of formula:

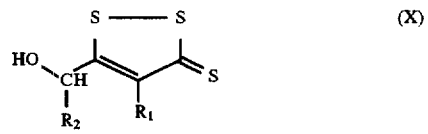

(X)

in which $R_1$ and $R_2$ have the meaning given in claim 1.

5. Composition according to claim 1, comprising, as active principle, a compound of formula:

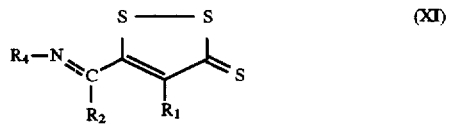

(XI)

in which $R_1$ and $R_2$ have the meaning given in claim 1 and $R_4$ represents a $C_1$–$C_6$ alkyl group or an aryl group.

6. Composition according to claim 1, comprising, as active principle, a compound of formula:

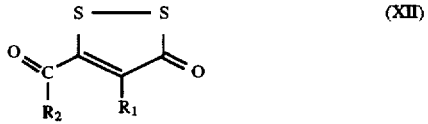

(XII)

in which $R_1$ and $R_2$ have the meaning given in claim 1.

7. A method for inhibiting platelet aggregation, comprising administering an amount of a compound according to claim 1, which is effective to inhibit platelet aggregation.

* * * * *